United States Patent [19]

Gerich et al.

[11] Patent Number: 4,819,636

[45] Date of Patent: Apr. 11, 1989

[54] MEDICAL DEVICE

[76] Inventors: Horst Gerich, 24034 Welby Way, Canoga Park, Calif. 91307; Thomas V. Meter, 9957 Stonehurst Ave., Sun Valley, Calif. 91352

[21] Appl. No.: 818,887

[22] Filed: Jan. 14, 1986

[51] Int. Cl.[4] .............................................. A61B 17/32
[52] U.S. Cl. .................................... 128/318; 128/321; 7/135
[58] Field of Search ....................... 128/321, 322, 318; 7/135

[56] References Cited

U.S. PATENT DOCUMENTS

| 3,648,701 | 3/1972 | Botts | 128/321 |
| 4,164,223 | 8/1979 | Munib | 128/321 |
| 4,452,244 | 6/1984 | Chin | 128/321 |

FOREIGN PATENT DOCUMENTS

| 2821893 | 12/1978 | Fed. Rep. of Germany | 128/321 |
| 1183358 | 7/1959 | France | 128/318 |
| 278763 | 2/1952 | Switzerland | 128/321 |

Primary Examiner—Michael H. Thaler

[57] ABSTRACT

A forcepslike device for cutting and squeezing tubing. The forceps comprise a pair of pivotally joined arms having cutting edges on one end to cut in a scissorlike fashion and finger engagable loops at the other end. A roller is mounted on each of the arms. The rollers are movable toward each other to grip a flexible plastic tube between them when the forceps are closed. The rollers have matching configuration to insure proper gripping of the tube to clear the tube of its contents.

5 Claims, 2 Drawing Sheets

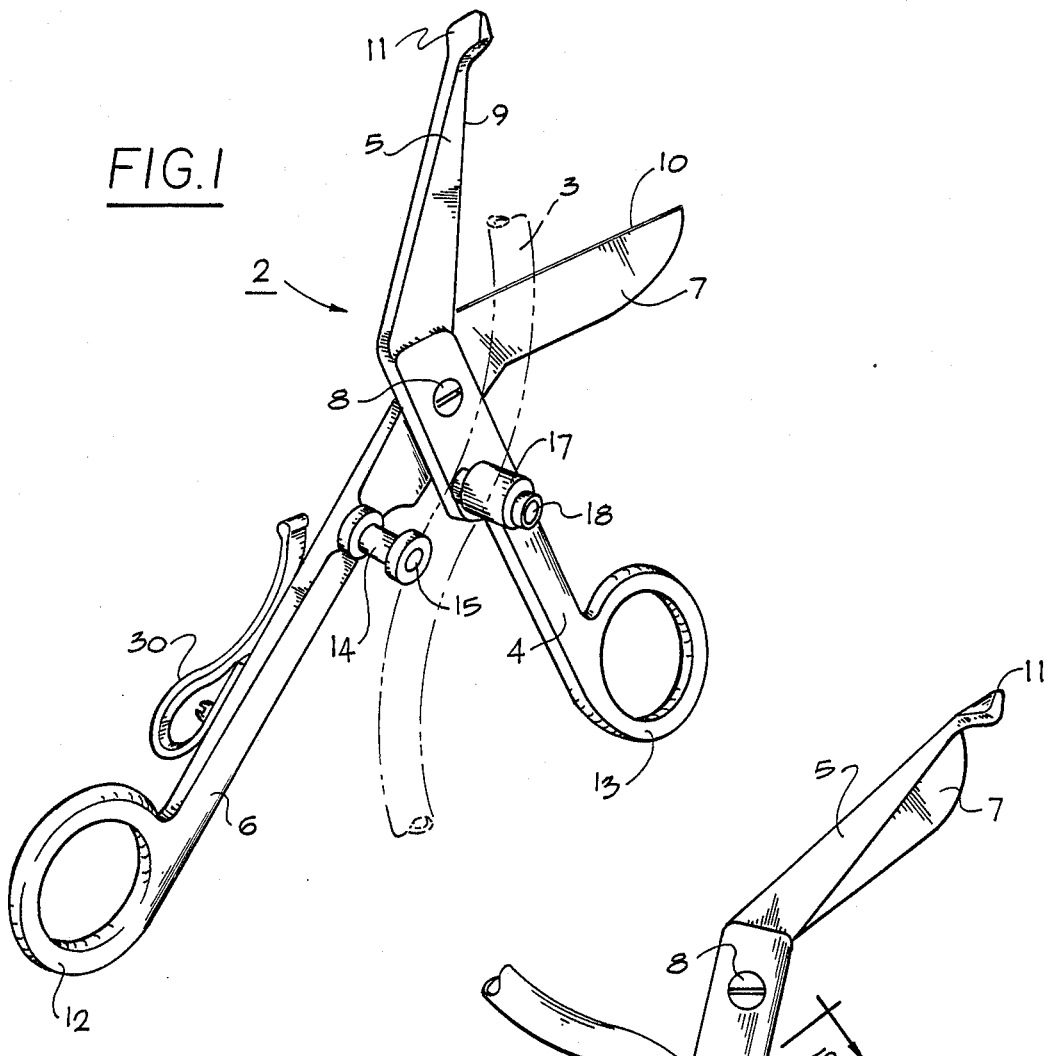

MEDICAL DEVICE

BACKGROUND OF THE INVENTION

The present invention relates to a forceps-like instrument useful for stripping the contents of flexible tubing and also for cutting tubing, bandages and the like. More particularly, the invention concerns hand operated scissors having a pair of rollers mounted thereon which are urged together on opposite sides of flexible tubing and pass lengthwise along the tubing to strip its contents.

Flexible tubing of rubber or plastic materials is widely used for medical purposes and it frequently becomes necessary to clear the contents of the tubing. For example, in blood transfusions it is desirable to clear all the blood from the tubing by stripping the tubing and either returning the blood to its source or delivering it to the patient. Blood is a very valuable commodity and its use must be handled carefully. During some types of hospital use such as intraveneous feeding it is necessary to eliminate the presence of air from the intraveneous apparatus. Also frequently tubing becomes clogged and it is necessary to clear the tubing while maintaining it in its proper position on the patient. The present invention is an aid in accomplishing these ends.

Hospital workers frequently carry scissors for cutting tubing, bandages and the like. It is desirable to combine various instruments into a single instrument thereby minimizing the weight that each individual worker must carry and also reducing the cost of the instruments used in a hospital. The present invention accomplishes this end.

SUMMARY OF THE INVENTION

Prior art devices for stripping flexible tubes are shown in U.S. Pat. Nos. 3,648,701; 4,164,223; 4,287,890 and 4,452,244. Such devices are functional in achieving the end result of collapsing and stripping the tubing but are rather cumbersome to carry and have parts that stick outwardly which engage pockets of the hospital workers clothing and ultimately result in tearing holes therein.

Also hospital workers are required to carry a variety of instruments to perform their duties and the present invention combined two functional instruments into one device thereby minimizing the weight carried by a worker and also reducing the cost of the device.

As a further object of the present invention to provide a tube stripping device wherein the rollers which engage the tubing are specifically designed for the purpose of stripping tubing and minimizing the possibility that the tubing will shift in the rollers which can result in cutting the tubing or forming weak spots therein.

BRIEF DESCRIPTION OF THE DRAWINGS

FIG. 1 is a prospective view of the device designed in accordance with the present invention, shown in open position;

FIG. 2 is a side elevation view of the device made according to the present invention;

DETAILED DESCRIPTION OF THE INVENTION

Figure 3:
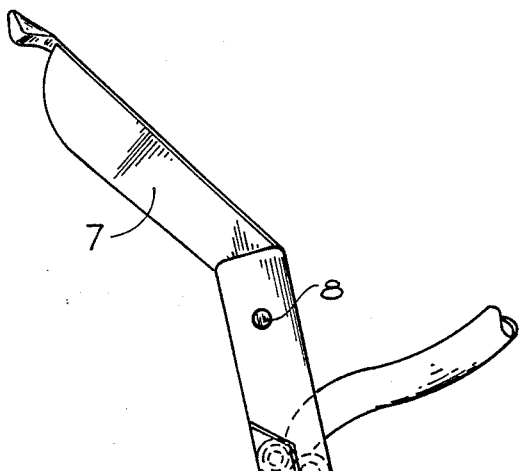
FIG. 3 is the side elevation view of the device made according to the invention and viewed from the opposite side of the device from FIG. 2.

Referring now to the drawings, the medical device 2 is shown with a length of tubing 3, pictured in a dotted outline, located within the device preparatory to clamping and stripping the tubing. FIGS. 2, 3, 5 and 6 show the tubing clamped between the rollers of the device and being stripped of its liquid contents.

The device 2 has a scissorlike construction and operation. It has a first arm consisting of a lower part 4 and an upper part 5, and a second arm consisting of a lower part 6 and an upper part 7. These arms are pivoted by a pivot axle 8 in the form of a pin or rivet which is slidably received in the arm 4 and is threadably and nonrotatably received in a hole in the arm 6. Thus the arms can pivot relative to each other as shown in FIGS. 1 and 2 about the pivot axle 8.

The arm 5 has an inwardly facing cutting edge 9 and the arm 7 has an inwardly facing cutting edge 10. These cutting edges engage each other during the pivoting of the arms 5 and 7 toward each other and function as conventional cutting scissors. An optional guide 11 is affixed to the outer end of arm 5 and is useful for inserting the cutting blade under bandages or the like which is well known in the art.

Arms 4 and 6 are pivotal about axle 8 toward and away from each other which results in simultaneous movement of the arms 5 and 7 toward and away from each other. Finger loops 12 and 13 are provided on the end of the arms 6 and 4 respectively and the users fingers are inserted in the loops 12 and 13 in manipulating the scissors open and shut.

A first roller 14 is affixed to arm 4 between the pivot point 8 and the end loops 13. This roller 14 is better seen in FIG. 5. The roller 14 is mounted on a pin 15 which allows free rotation of the roller 14 about the pin and relative to the arm 4. The axis of rotation of the roller 14 is parallel to the axle 8 in the preferred embodiment shown in these drawings. However, these axes could be at different angles and still provide the same function described herein.

The roller 14 has a center cylindrical surface 13 and end flanges 16 which extend radially outwardly from the axis 15 and surface 13. The first roller has the appearance similar to a spool.

Figure 5:
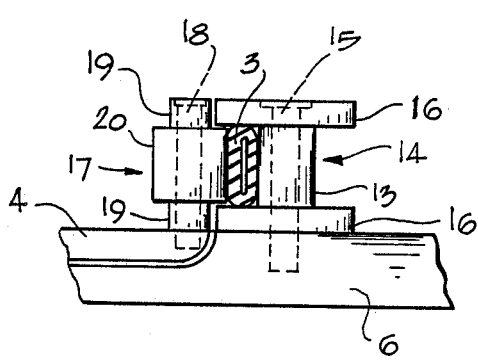
FIG. 5 is a cross-sectional view taken on line 5-5 of FIG. 2.

A second roller 17 is mounted on a pin 18. The axis pin 18 is parallel to pin 15. The pin 18 is rigidly mounted in the arm 6 and the roller 17 is rotatable about the pin 18 and relative to arm 6. As shown in FIG. 5 the roller 18 has a center portion 20 which is cylindrical and extends outwardly from the pin 18 in a radial direction greater than the end portions 19 of the roller 17.

Also as shown in FIG. 5 the flanges 16 on roller 14 extend within the recessed portions 19 of roller 17 when the rollers are properly pressed together with the tubing 3 between. This configuration insures that the tubing will remain within the central portion in engagement with surface 13 thereby avoiding tube pinching.

Figure 6:
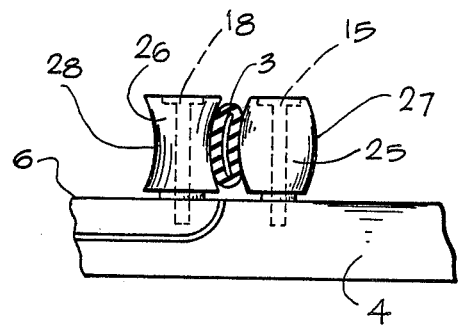
FIG. 6 is a view similar to FIG. 5 but showing a modified form of the rollers.
Figure 4:
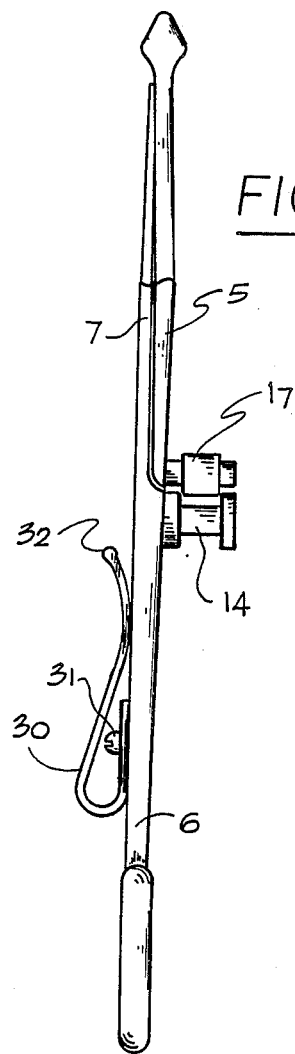
FIG. 4 is a side elevation view taken from the left-hand side of FIG. 2.

FIG. 6 shows a modified form of the rollers. Roller 25 is rotatively mounted on the pin 15 and is rotateable thereabout and relative to arm 4. The roller 26 is rotatively mounted on pin 18 and is rotateable thereabout and relative to arm 6. The outer surface of roller 25 is continuous and has a barrel like shaped surface 27. The surface 27 is a surface of revolution about the pin 15.

The roller 26 has a surface 28 which is concave inwardly toward the axis of rotation 18. Ideally the surfaces 28 and 27 are complimentary thus evenly squeezing the tube 3 between them as shown in FIG. 6.

The rollers shown in FIG. 5 are the preferred embodiment of the present invention in that the tubing 3 is trapped between the rollers by the outward extending flanges 16 on roller 14 and the risk of pinching the tubing 3 during stripping is substantially reduced. The rollers shown in FIG. 6 function well if the configuration of the surfaces 27 and 28 are sufficiently deep to maintain the tubing 3 between the rollers during stripping without risk of pinching.

The present invention also includes a spring clamp 30 which is affixed by a screw 31 to the backside of arm 6. This spring clamp 30 is spring biased toward the arm 6 and its loose end 2 may be swung outwardly from arm 6. Thus the spring clamp 30 allows the worker to place the device in his pocket with the spring clamp looped over the pocket edge to retain the device within the pocket.

In operation, the device is gripped by the operator placing his fingers in loops 12 and 13 and opened to a position shown in FIG. 1. The device may then either be used as a pair of scissors utilizing the cutting edges 9 and 10 or as a tube stripper utilizing the rollers 14 and 17. When used as a tube stripper, a length of tubing is inserted between the rollers 17 and 14 in the manner shown in FIG. 1. The rollers should be transversed to the length of tubing and the device is in the position shown in FIG. 2, with sufficient force to compress the tubing walls together as shown in FIG. 5. Thereupon the operator pulls the device along the length of tubing, applying sufficient pressure to the rollers to cause the entire contents of the tubing to be forced in the direction that the device is moved. It should be noted that when the arms of the device are completely pressed together by the user the flange 16 will engage the recessed portion 19 of roller 17. The scissors normally have a gap 32 between the arms 6 and 4. It is important that the rollers be permitted to come into engagement between the flange 16 and the recessed portion 19. At that point the cutting edges 9 and 10 have performed their function of cutting.

It should be noted that the configuration of the present invention may be otherwise embodied in a useful instrumentality which is somewhat different from the device shown and described herein but this modified device falls within the full spirit of the present invention and is intended to be covered hereby.

We claim:

1. A medical device for cutting and squeezing tubing comprising:
   a pair of elongated arm members; integral pivot means connecting the arm members together for movement relative to each other about a single fixed pivot axis, said pivot axis of the pivot means extending transversely of the arm members at a point between the ends of the arm members,
   each arm member having a first end remote from the pivot means, said first end on each arm member being movable toward and away from the other first end, each of said first ends having a cutting edge, so that the arms may pivot toward each other in a scissor cutting action about the pivot means;
   each arm member having a second end remote from the pivot means, said second end on each arm member being movable toward and away from the other second end, each of said second ends having an area engageable by a user's fingers to move the ends toward each other in a scissor action about the pivot means;
   first and second rollers mounted rotatably on individual axes affixed to said arm members between said pivot means and said second ends; each of said axes being affixed to a different arm member; said axes being substantially parallel to each other and to said pivot axis of the pivot means,
   whereby when the user's fingers engage said second ends and squeeze them together, said cutting edges engage each other in said cutting action and the rollers move toward each other until they reach a fixed position relative to each other sufficient to permit tubing to be squeezed between the rollers.

2. A device according to claim 1 wherein said first roller has a central portion dished inwardly toward its axis, and end portions extending radially outward from the axis, to provide a continuous hollow central area on the roller; and said second roller having a central portion raised outwardly and radially from its axis and end portions recessed radially inward toward its axis; the raised central portion of the second roller generally conforming in shape to said hollow central area on the first roller; such that tubing is readily retained within the hollow area by the second roller when squeezing the tubing.

3. A device according to claim 2 wherein said end portions on said first roller engage the end portions of said second roller when the tubing is squeezed between the rollers.

4. A device according to claim 2 wherein said first roller has a continuous surface concave inward toward its axis of rotation, and said second roller has a continuous surface convex outwardly away from its axis of rotation, said concave and convex surfaces being substantially complementary to each other.

5. A device according to claim 1 wherein when said second ends are squeezed together, said first ends engage each other to a stop position.

* * * * *